(12) United States Patent
McKinnon et al.

(10) Patent No.: US 8,257,313 B2
(45) Date of Patent: Sep. 4, 2012

(54) INTEGRATED SEPTUM AND NEEDLE TIP SHIELD FOR A CATHETER ASSEMBLY

(75) Inventors: Austin Jason McKinnon, Herriman, UT (US); Jeffrey Charles O'Bryan, Murray, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 314 days.

(21) Appl. No.: 11/503,237

(22) Filed: Aug. 11, 2006

(65) Prior Publication Data

US 2008/0097344 A1      Apr. 24, 2008

(51) Int. Cl.
*A61M 5/178* (2006.01)
(52) U.S. Cl. .............. 604/164.08; 604/164.01; 604/263
(58) Field of Classification Search ............. 604/164.01, 604/164.07, 164.08, 110, 167.01, 167.02, 604/192, 198, 263
See application file for complete search history.

(56) References Cited

U.S. PATENT DOCUMENTS

| | | | |
|---|---|---|---|
| 4,846,809 A * | 7/1989 | Sims | 604/198 |
| 4,964,854 A * | 10/1990 | Luther | 604/166.01 |
| 5,328,482 A | 7/1994 | Sircom et al. | |
| 5,458,658 A | 10/1995 | Sircom | |
| 5,584,809 A | 12/1996 | Gaba | |
| 5,599,310 A | 2/1997 | Bogert | |
| 5,755,709 A | 5/1998 | Cuppy | |
| 5,865,806 A * | 2/1999 | Howell | 604/164.12 |
| 6,083,203 A * | 7/2000 | Yoon | 604/167.01 |
| 6,117,108 A | 9/2000 | Woehr | |
| 6,224,569 B1 | 5/2001 | Brimhall | |
| 6,287,278 B1 | 9/2001 | Woehr et al. | |
| 6,595,954 B1 | 7/2003 | Luther et al. | |
| 6,616,630 B1 | 9/2003 | Woehr et al. | |
| 6,652,486 B2 | 11/2003 | Bialecki et al. | |
| 6,692,471 B2 * | 2/2004 | Boudreaux | 604/198 |
| 6,699,221 B2 | 3/2004 | Vaillancourt | |
| 7,347,838 B2 * | 3/2008 | Kulli | 604/164.08 |
| 2002/0026154 A1 | 2/2002 | Chang | |
| 2002/0169418 A1 | 11/2002 | Menzi | |
| 2003/0195471 A1 | 10/2003 | Woehr | |
| 2004/0204689 A1 | 10/2004 | Lynn | |
| 2004/0225260 A1 | 11/2004 | Villa et al. | |

(Continued)

FOREIGN PATENT DOCUMENTS

JP         07-148270         6/1995

(Continued)

OTHER PUBLICATIONS

The Notification of the First Office Action, dated Oct. 19, 2011, from the State Intellectual Property Office of the People's Republic of China.

(Continued)

*Primary Examiner* — Kevin C Sirmons
*Assistant Examiner* — Laura C Schell
(74) *Attorney, Agent, or Firm* — Kinney & Lange, P.A.

(57) ABSTRACT

An integrated septum and needle tip shield for use in a catheter assembly includes a septum configured to removably engage with an inner surface of a catheter hub and a tip shield secured inside the septum. The tip shield is configured to move between an open position in which a tip of a needle is distal of the tip shield and a closed position in which the tip of the needle is protected inside the tip shield.

15 Claims, 8 Drawing Sheets

U.S. PATENT DOCUMENTS

2005/0277879 A1    12/2005    Daga

FOREIGN PATENT DOCUMENTS

| | | |
|---|---|---|
| JP | 2001218844 A | 8/2001 |
| JP | 2002320674 A | 11/2002 |
| JP | 2003510137 A | 3/2003 |
| JP | 2004528127 A | 9/2004 |
| JP | 2004535905 A | 12/2004 |
| WO | WO2005/079891 | * 9/2005 |
| WO | WO2005079891 A1 | 9/2005 |

OTHER PUBLICATIONS

The Official Notice of Rejection mailed Feb. 14, 2012 from the Japanese Patent Office for Japanese Patent Application No. 2009-524623.

* cited by examiner

INTEGRATED SEPTUM AND NEEDLE TIP SHIELD FOR A CATHETER ASSEMBLY

BACKGROUND OF THE INVENTION

The present invention relates to a catheter assembly. In particular, the present invention relates to an integrated septum and needle tip shield for use in a catheter assembly.

Intravascular catheters are used for infusing fluid into a patient, withdrawing fluid from a patient, or monitoring various parameters of the patient's vascular system. Typically, a needle is used to introduce the catheter into a patient's blood vessel. A catheter is mounted over a needle that has a sharp distal tip with at least the distal portion of the catheter tightly engaging the outer surface of the needle to prevent peel-back of the catheter during insertion into the blood vessel.

A clinician inserts the needle through the patient's skin and into the patient's blood vessel. Once a flashback of blood is seen within a flashback chamber, the catheter is threaded over the needle and inserted completely into the blood vessel. The needle is then withdrawn from the catheter leaving the catheter in place. Once the needle is withdrawn from the catheter, the needle is a "blood-contaminated sharp" and must be properly handled.

In recent years, there has been great concern over accidental needle sticks by blood-contaminated sharps. Despite awareness of the need to properly handle blood-contaminated sharps, accidental needle sticks with contaminated needles still occur, for example, during emergency situations or as a result of inattention or neglect. As a result of this problem, various needle shields have been developed. Besides protecting clinicians from accidental needle sticks, needle shields should also minimize exposure to blood throughout the catheter insertion process.

One disadvantage of many needle shield designs is that they have sharp, exposed metal edges. Moreover, because the needle shield is very small, it is hard for a clinician to visually confirm whether a tip of the needle is protected. In some designs, even if the needle tip is protected, the clinician may still be exposed to blood spillage from the catheter hub during the catheter insertion process and/or to blood splatter caused by blood residing on the needle as the needle is withdrawn.

There is a need for a needle shield that protects a clinician from exposure to sharp metal edges and provides quick visual confirmation that the clinician is protected from a needle stick, while also providing blood containment during insertion of the catheter and withdrawal of the needle.

BRIEF SUMMARY OF THE INVENTION

The present invention relates to an integrated septum and needle tip shield apparatus for use in a catheter assembly having a needle, a catheter and a catheter hub. The apparatus includes a septum configured to removably engage with an inner surface of the catheter hub, and a tip shield secured inside the septum and configured to move between an open position in which a tip of the needle is distal of the tip shield and a closed position in which the tip of the needle is protected inside the tip shield. The apparatus is secured inside the catheter hub until the tip of the needle is inside the tip shield, at which point the apparatus is easily removable from the catheter hub with the needle.

DETAILED DESCRIPTION

Figure 1:
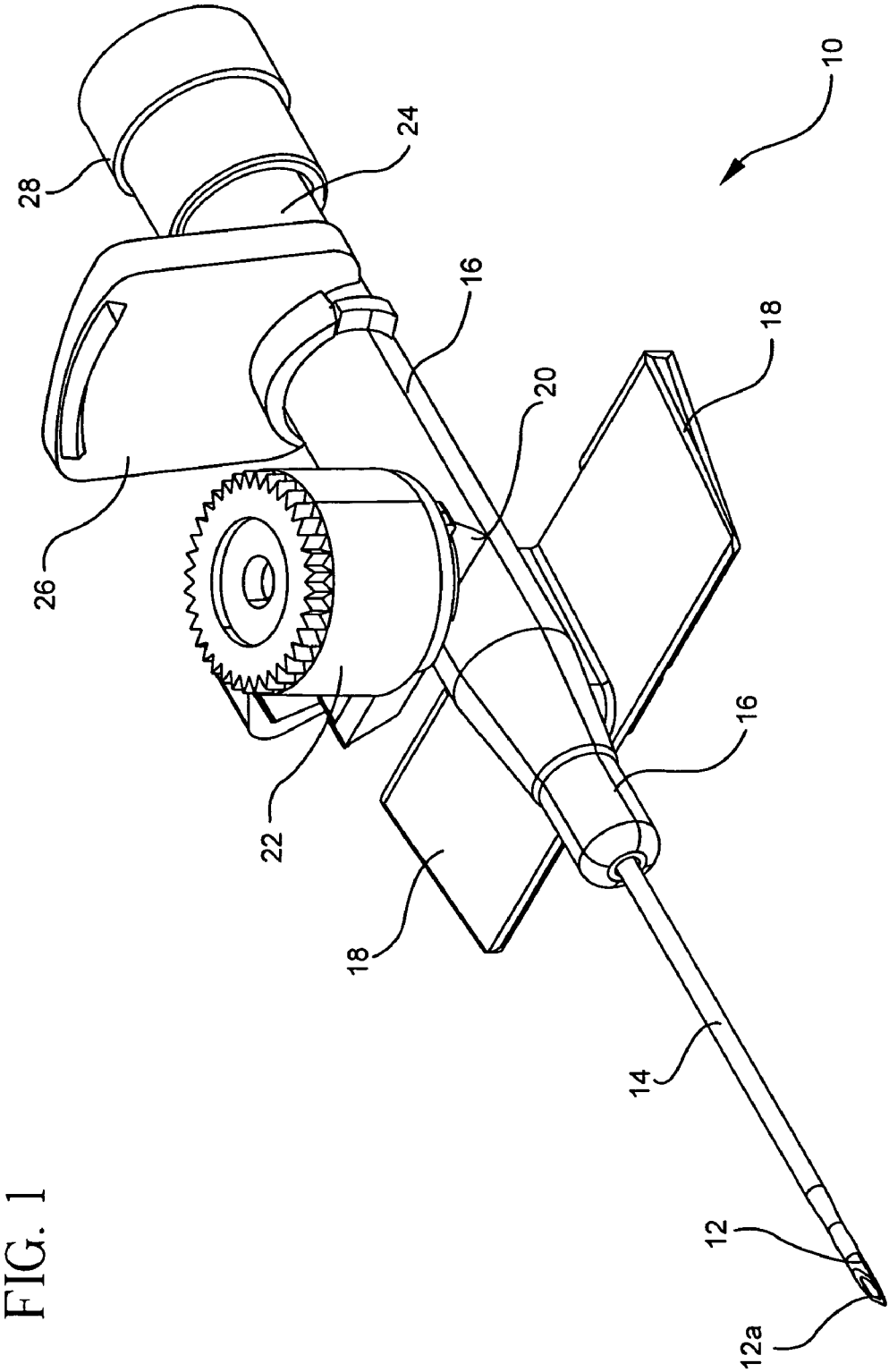
FIG. 1 is a perspective view of a representative embodiment of a catheter assembly prior to insertion of a catheter.

FIG. 1 is a perspective view of a representative embodiment of catheter assembly 10 prior to placement in a blood vessel of a patient. Catheter assembly 10 includes needle 12 having needle tip 12a and feature on the needle 13 (shown in FIG. 2), catheter 14, catheter hub 16, wings 18, port 20 shown with cap 22 inserted over port 20, needle hub 24 having grip member 26, and vent plug 28. The distal end of catheter assembly 10 is generally toward needle tip 12a and the proximal end is generally toward vent plug 28.

Figure 2:
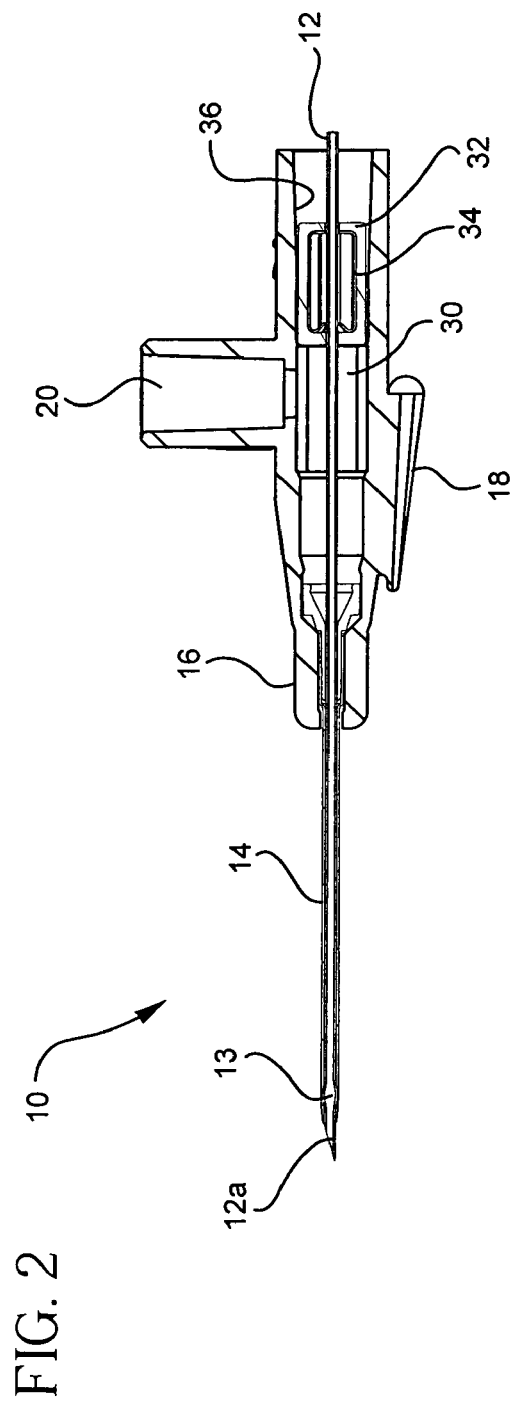
FIG. 2 is a sectional view of the catheter assembly of FIG. 1.

FIG. 2 is a sectional view of catheter assembly 10 of FIG. 1. In FIG. 2, cap 22, needle hub 24 and vent plug 28 have been removed for clarity. As shown in FIG. 2, catheter hub 16 includes port septum 30, integrated septum 32 and tip shield 34. Tip shield 34 is completely enclosed within septum 32 such that septum 32 and tip shield 34 form an integrated unit which may be inserted and securable inside catheter hub 16, yet be easily removed from catheter hub 16 at an appropriate time (as explained below). As shown in FIG. 2, septum 32 and tip shield 34 are positioned inside catheter hub 16 and configured such that needle 12 passes through an opening in septum 32 and tip shield 34. As explained in more detail below, tip shield 34 is configured to flex between an open and a closed position. In FIG. 2, tip shield 34 is in the open position due to a spreading force exerted on tip shield 34 by needle 12. Tip shield 34 remains in the open position until needle 12 is withdrawn to a position where needle tip 12a is enclosed inside tip shield 34. When tip shield 34 is in the open position, septum 32 is configured to engage with inner surface 36 of catheter hub 16, thus creating a seal to contain blood inside catheter hub 16. In preferred embodiments, septum 32 is formed from an expandable material, as described further below, and is soft and pliable.

Needle 12 is inserted through the patient's skin into a blood vessel. Placement of needle 12 in a blood vessel is verified by confirming that there is a flashback of blood visible in needle hub 24 and vent plug 28 (see FIG. 1). Needle 12 is then withdrawn from catheter 14 by using grip member 26 to pull needle hub 24 and vent plug 28 in a proximal direction from catheter hub 16, leaving catheter 14 in place in the patient's blood vessel.

Figure 3:
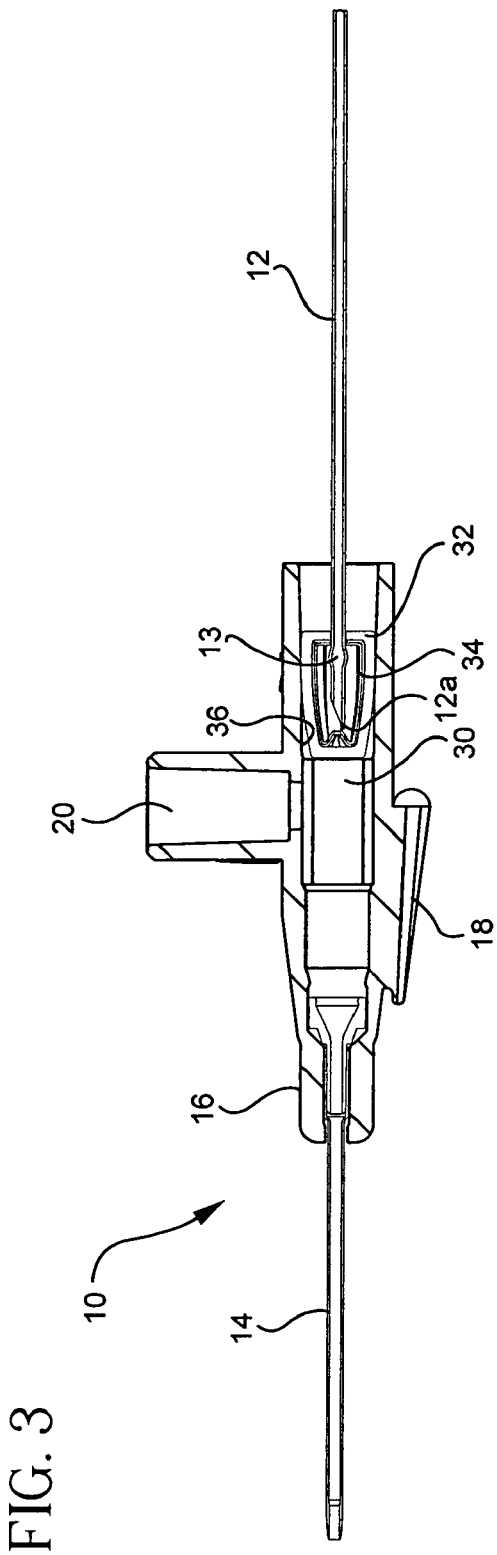
FIG. 3 is a sectional view of the catheter assembly of FIG. 2 after insertion of the catheter and as a needle is being withdrawn.

FIG. 3 is a sectional view of catheter assembly 10 of FIG. 2 after needle 12 has been withdrawn from catheter 14, but before needle 12 is completely withdrawn from catheter hub 16. As shown in FIG. 3, tip shield 34 is in a closed position and septum 32 has disengaged from inner surface 36 of catheter hub 16. As explained in greater detail below, tip shield 34 moves from the open position (FIG. 2) to the closed position immediately after needle tip 12a is past a distal end of tip shield 34. Tip shield 34 automatically closes because needle 12 is no longer exerting a spreading force against tip shield 34 to hold it open. When tip shield 34 moves to the closed position, in preferred embodiments, septum 32 returns to its original shape and correspondingly disengages from inner surface 36 of catheter hub 16, such that septum 32 and tip shield 34 are easily removed from catheter hub 16. At this point, needle 12 may be completely removed from catheter hub 16 with tip shield 34 and septum 32 secured around needle tip 12a.

As shown in FIG. 3, needle 12 may include feature 13 located on a distal portion of needle 12, but in a proximal location relative to needle tip 12a. Feature 13 results in needle 12 having an increased diameter at a specific location on needle 12. As needle 12 is being withdrawn from catheter hub 16, needle 12 is prevented from further proximal movement when feature 13 reaches a proximal end of tip shield 34. Thus, needle tip 12a is secured inside tip shield 34 and septum 32. Any subsequent pulling force results in septum 32 and tip shield 34 being removed from catheter hub 16 with needle 12.

Although a bump is shown in FIG. 3 as feature 13 on needle 12, it is recognized that any type of feature may be used on needle 12, so long as it is configured to prevent needle 12 from passing completely through tip shield 34 and septum 32.

Catheter assembly 10, as described in reference to FIGS. 1-3, is designed to create an interlock between catheter hub 16 and the integrated unit of septum 32 and tip shield 34 such that septum 32 is held in place inside catheter hub 16, creating a blood-containing seal, until needle tip 12a is safely contained within tip shield 34. Once needle tip 12a is confined within tip shield 34, septum 32 automatically releases itself from engagement with inner surface 36 of catheter hub 16. At that point, septum 32 may easily be removed from catheter hub 16. It is not required that septum 32 completely disengage from inner surface 36 of catheter hub 16 once tip shield 34 is in the closed position, so long as there is some reduction in engagement force with catheter hub 16 as compared to when tip shield 34 is in the open position. The reduction in engagement force allows septum 32 to be removed from catheter hub 16 as needle 12 is withdrawn.

Catheter assembly 10 is shown in FIGS. 1-3 as being a ported catheter with port 20 which may be used for delivering fluids through catheter 14. However, it is recognized that the present invention of an integrated septum and needle tip shield may be used with any type of catheter assembly, including a straight catheter. If a straight catheter were substituted in catheter assembly 10, in place of the ported catheter of FIGS. 1-3, port septum 30 may not be needed since its primary purpose is to prevent fluids from leaking out of port 20. The catheter assembly of the present invention, having an integrated septum and tip shield, is designed to contain blood and other fluids within catheter hub 16 during insertion of catheter 14, while also providing improved needle tip-shield capabilities when needle 12 is removed after the insertion of catheter 14.

Once needle 12 is completely withdrawn from catheter hub 16, with septum 32 and tip shield 34 enclosed around needle tip 12a, the clinician may control the flow of blood (in a proximal direction) through and out of catheter hub 16 in various, commonly known ways. For example, the clinician may manually apply pressure to a vein that catheter 14 is inserted into to prevent blood flow. In addition to or as an alternative, the clinician may mount a cap onto catheter hub 16 to block blood from flowing out of catheter hub 16. It is also common for the clinician to instead attach an IV line to catheter hub 16.

Figure 4:
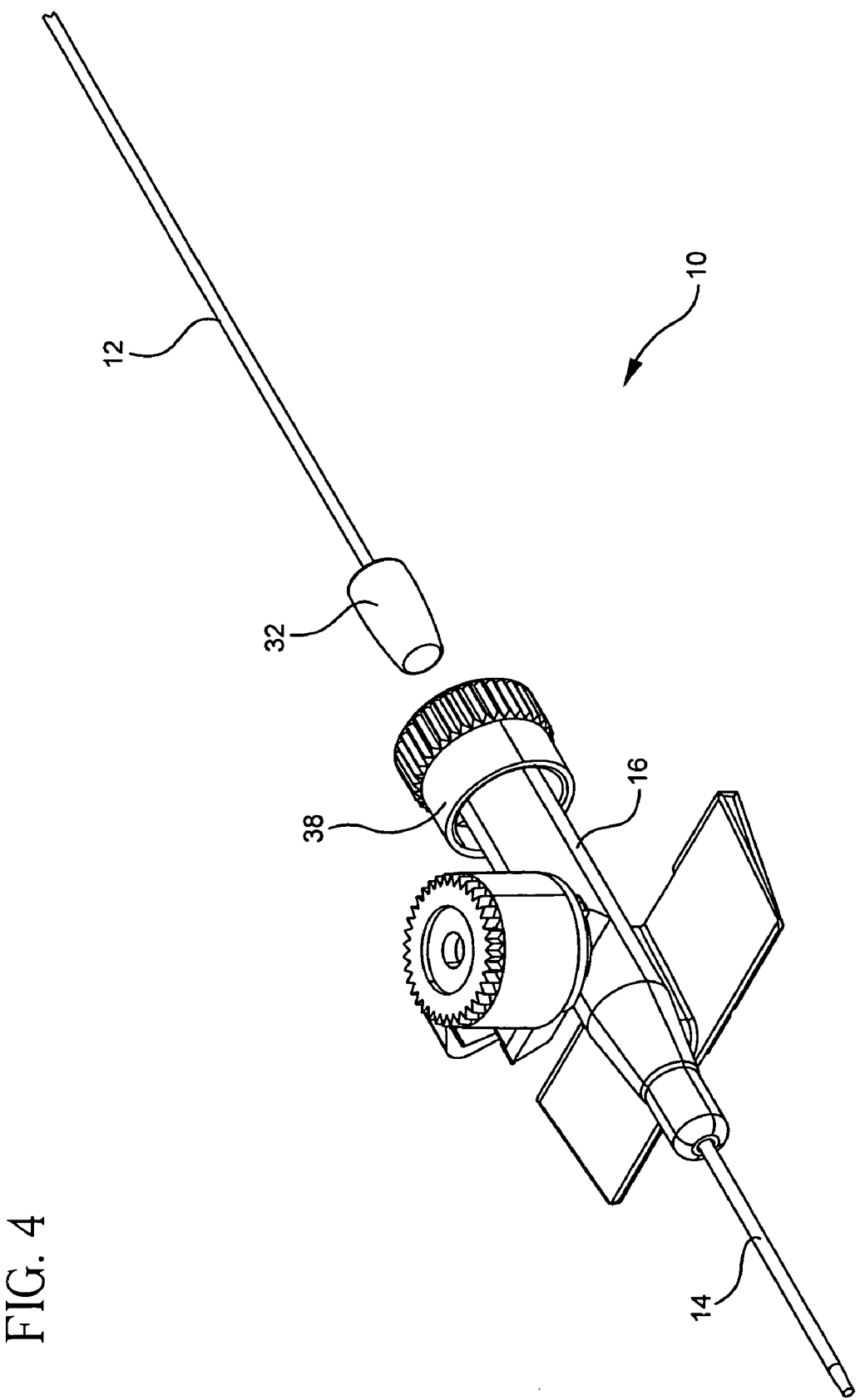
FIG. 4 is a perspective view of the catheter assembly of FIG. 1 after an integrated septum and needle tip shield is withdrawn from a catheter hub and a cap has been inserted on the catheter assembly.

FIG. 4 is a perspective view of catheter assembly 10 of FIGS. 1-3 after needle 12 has been completely withdrawn from catheter hub 16 and cap 38 has been inserted onto a proximal end of catheter hub 16. Cap 38 functions to seal any blood or other fluids inside catheter hub 16. Cap 38 is illustrated as one example for preventing blood leakage from catheter hub 16; however, as mentioned above, there are a variety of ways to control blood flow. As one possible alternative to cap 38, the clinician may instead insert a luer fitting that is configured for receiving an IV line. As shown in FIG. 4, when needle 12 is completely withdrawn from catheter hub 16, needle tip 12a is protected inside tip shield 34 which is completely enclosed by septum 32.

Figure 5:
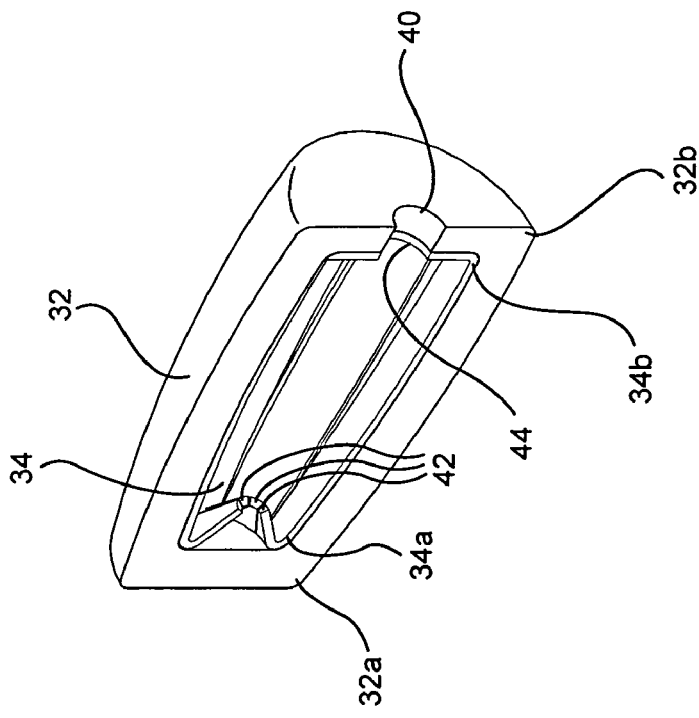
FIG. 5 is a perspective view, in section, of a representative embodiment of an integrated septum and tip shield used in the catheter assembly of FIGS. 1-4.

FIG. 5 is a perspective view, in section, of septum 32 and tip shield 34 of FIGS. 2-4, in the closed position. As mentioned above, in preferred embodiments, tip shield 34 is completely enclosed within septum 32. Septum 32 includes distal end 32a and proximal end 32b, and opening 40. Tip shield 34 similarly includes distal end 34a and proximal end 34b, and with a plurality of resilient fingers 42 at distal end 34a and opening 44 at proximal end 34b. Opening 40 of septum 32 and opening 44 of tip shield 34 are both slightly larger than an average outer diameter of needle 12, but less than the increased diameter of needle 12 at bump 13. As shown in FIG. 2, septum 32 is configured to expand and engage with inner surface 36 of catheter hub 16. Since proximal end 32b of septum 32 is essentially enclosed, except for opening 40 which receives needle 12, septum 32 functions to seal blood or other fluids inside catheter hub 16 during an insertion process of catheter 14. Needle 12 may be partially withdrawn from catheter 14, with needle tip 12a distal of tip shield 34, and septum 32 continues to function as a blood containment device. Thus, a clinician may perform other functions without first having to fully withdraw needle 12.

Distal end 32a of septum 32 may be pre-slit such that it is configured to create an opening when needle 12 is received through septum 32 and tip shield 34. The opening may be slightly larger than the diameter of needle 12. Because septum 32 may be formed from an elastomeric material, septum 32 may be designed such that once needle tip 12a is secured inside tip shield 34, any opening at distal end 32a closes. Thus, any residue of blood on needle 12 may be contained within septum 32 as needle 12 is withdrawn and passed through septum 32. It is also recognized that distal end 32a of septum 32 may be designed with a larger opening that may or may not seal closed after needle tip 12a is contained within tip shield 34.

In preferred embodiments, septum 32 may be formed from an elastomeric material, such as silicone or rubber, so that septum 32 is configured to be expandable. When needle 12 is received through tip shield 34 and fingers 42 of tip shield 34 are pushed outward by needle 12, septum 32 also expands outward. Once fingers 42 spring back to the closed position, as shown in FIG. 5, septum 32 may be designed to retract back to its original position.

In preferred embodiments, septum 32 completely encloses tip shield 34 both prior to insertion of catheter 14 into a vessel and after catheter 14 has been inserted and needle 12 has been withdrawn from catheter hub 16. Thus, a clinician or other users are not exposed to any sharp metal edges on tip shield 34 since it is enclosed within septum 32, which is made of rubber or another type of elastomer. Moreover, because septum 32 is larger than tip shield 34 and may be bright in color, septum 32 provides quick visual confirmation to a clinician that, when needle 12 is withdrawn from catheter hub 16, needle tip 12a is protected. This is illustrated in FIG. 4 which shows septum 32 enclosed around needle tip 12a.

Figure 6:
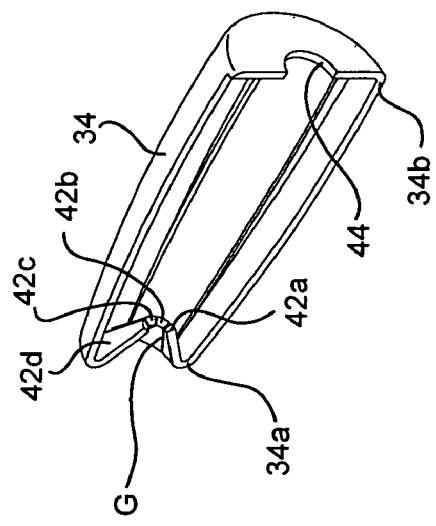
FIG. 6 is a perspective view, in section, of the tip shield of FIG. 5.

FIG. 6 is a perspective view, in section, of tip shield 34 of FIG. 5 in the closed position. In the embodiment shown in FIG. 6, tip shield 34 has a total of seven resilient fingers. Because FIG. 6 is a sectional view of tip shield 34, four of the seven fingers (42a, 42b, 42c and 42d) are visible in FIG. 6, although only half of finger 42d is shown. Tip shield 34 is configured such that, when plurality of fingers 42 are in the closed position, there is an opening at distal end 34a of tip shield 34. The opening has a diameter that is less than an outer diameter of needle 12. Thus, once a distal portion of needle 12, including tip 12a and bump 13, is inside tip shield 34, needle 12 is restrained from movement in the distal direction by fingers 42 which have closed around it. As discussed above, needle 12 is restrained from further movement in the proximal direction by bump 13.

Although the embodiment of tip shield 34 shown in FIGS. 2-6 has seven fingers, it is recognized that more or less fingers may be used in tip shield 34. Fingers 42 are configured such that gaps G (see FIG. 6) between each finger 42 are small enough to inhibit needle tip 12a from penetrating one of gaps G after needle tip 12a is inside tip shield 34.

Tip shield 34 may be formed from a metal, such as stainless steel. However, it is recognized that tip shield 34 may be made out of other materials, such as polycarbonate or other types of plastics.

Figure 7:
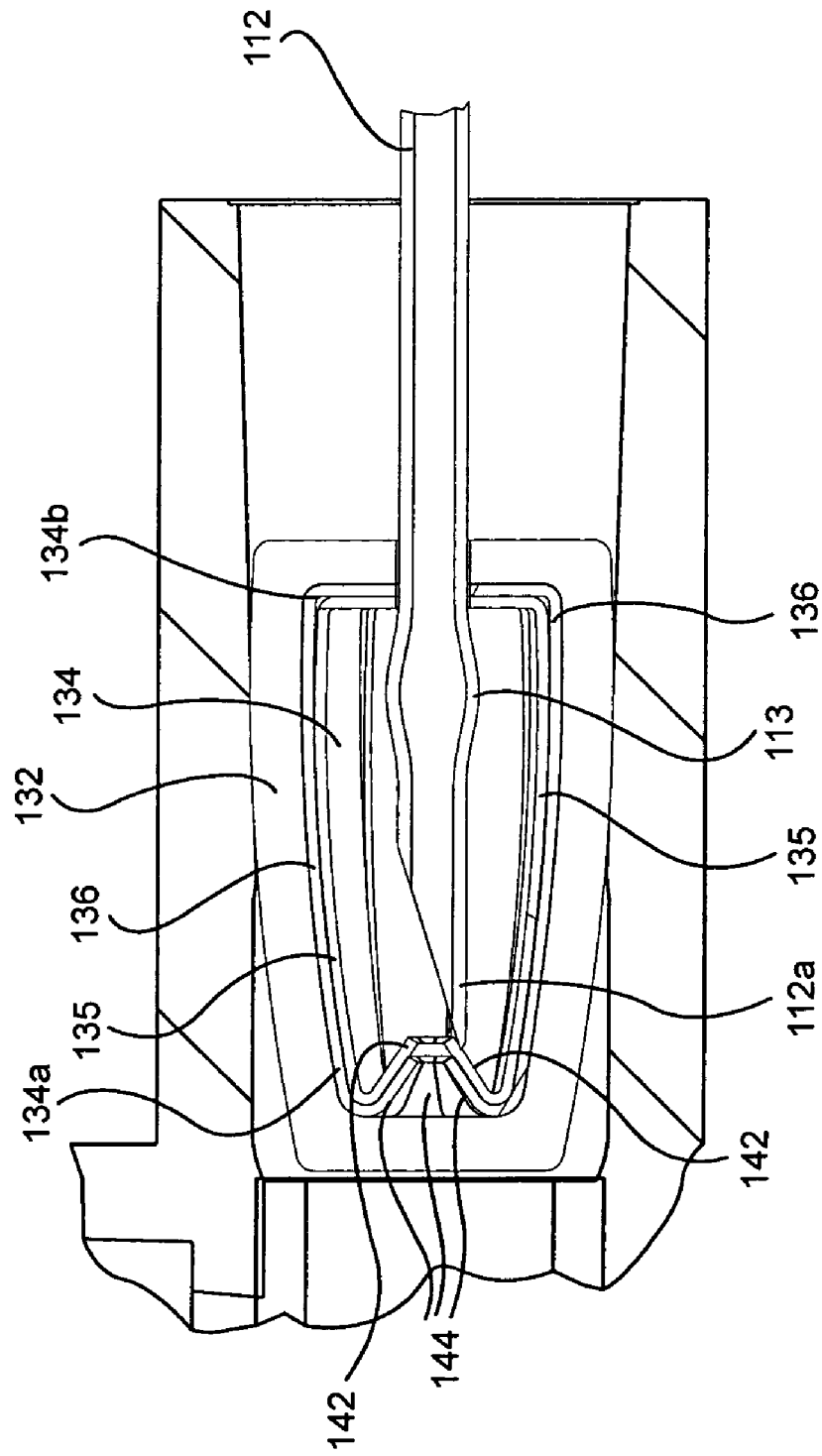
FIG. 7 is a sectional view of another embodiment of an integrated septum and tip shield for use in a catheter assembly.

FIG. 7 is a sectional view of another embodiment of an integrated septum and tip shield of the present invention, which includes septum 132 and tip shield 134 in a closed position. Similar to the embodiment described above and shown in FIGS. 2-6, in the embodiment of FIG. 7, tip shield 134 is completely enclosed inside septum 132. As shown in FIG. 7, needle 112, including needle tip 112a and feature 113, has been withdrawn through a portion of a catheter assembly and tip 112a and feature 113 are enclosed inside tip shield 134. As explained above, feature 113 functions to secure needle tip 112a within tip shield 134 and prevent needle 112 from being completely withdrawn through septum 132 and tip shield 134.

Tip shield 134 includes distal end 134a, proximal end 134b, inner body portion 135 and outer body portion 136. As shown in FIG. 7, outer body portion 136 is enclosed around inner body portion 135. Inner body portion 135 is similar to tip shield 34 of FIG. 6, and outer body portion 136, having a similar structure, is larger than inner body portion 135. Inner body portion 135 includes a plurality of resilient fingers 142 at distal end 134a. Outer body portion 136 includes a plurality of resilient fingers 144 which are configured to lay over fingers 142, as shown in FIG. 7.

Figure 8:
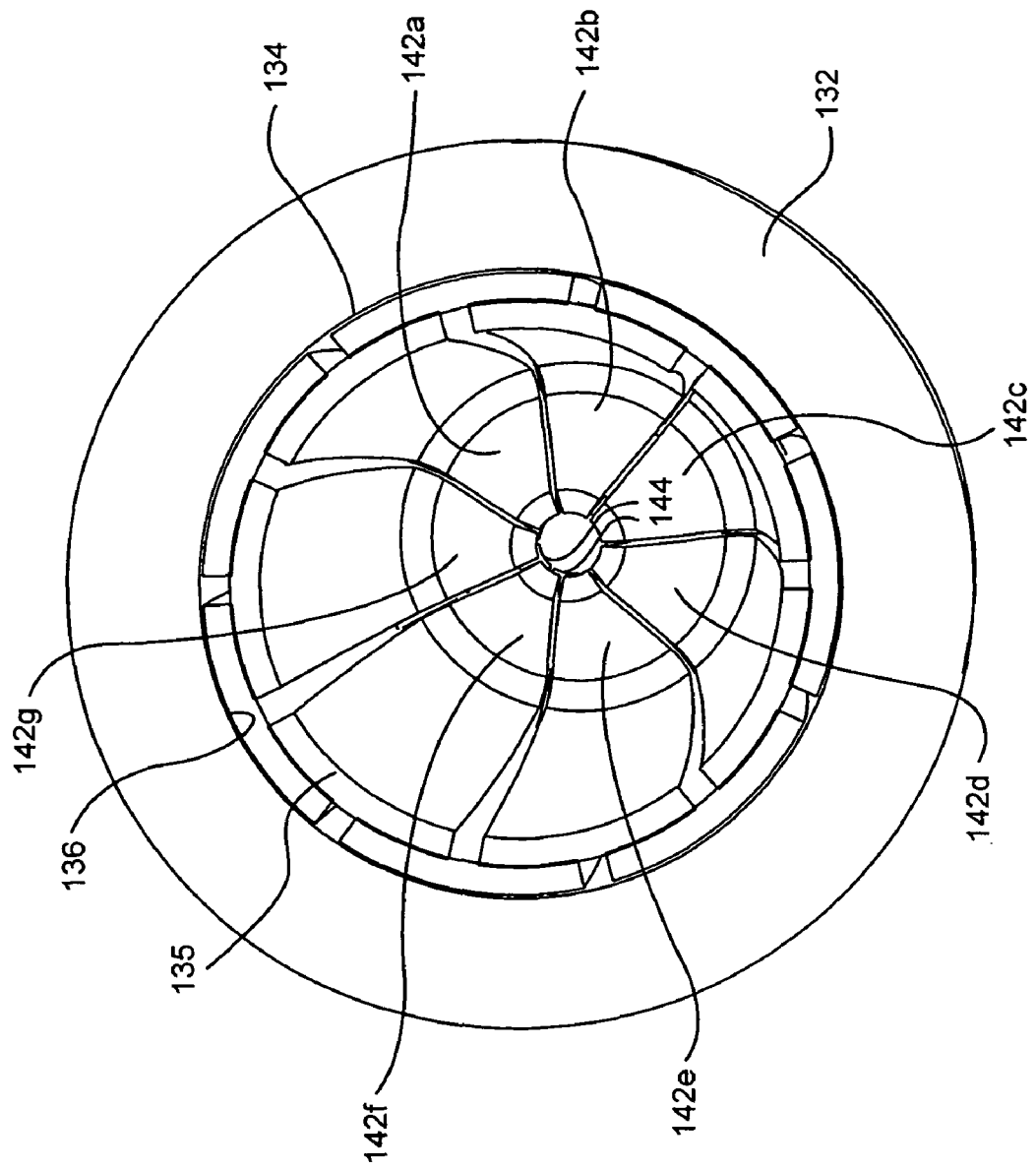
FIG. 8 is a perspective view, in section, of the integrated septum and tip shield of FIG. 7.

FIG. 8 is a perspective view, in section, of the integrated unit of septum 132 and tip shield 134 of FIG. 7, showing tip shield 134 in the closed position. As shown in FIG. 8, inner body portion 135 nests inside outer body portion 136. In the embodiment of tip shield 134 shown in FIGS. 7 and 8, inner body portion 135 and outer body portion 136 both have seven fingers each. Fingers 142a-142g of inner body portion 135 are shown in FIG. 8 at distal end 134a of tip shield 134. A small portion of some of fingers 144 of outer body portion 136 are visible in FIG. 8, located distally of fingers 142. As shown in FIG. 8, fingers 142 and 144 are offset from one another, such that gaps between each layer of fingers are also offset from one another.

As shown in FIG. 8, when tip shield 134 is in the closed position, there is an opening at distal end 134a. This opening is smaller than an outer diameter of needle 112 of FIG. 7. Once needle tip 112a is inside tip shield 134, needle 112 is unable to pass through the opening or pierce through any gaps in fingers 142 due to the double layer configuration of fingers 142 and 144.

Figure 9:
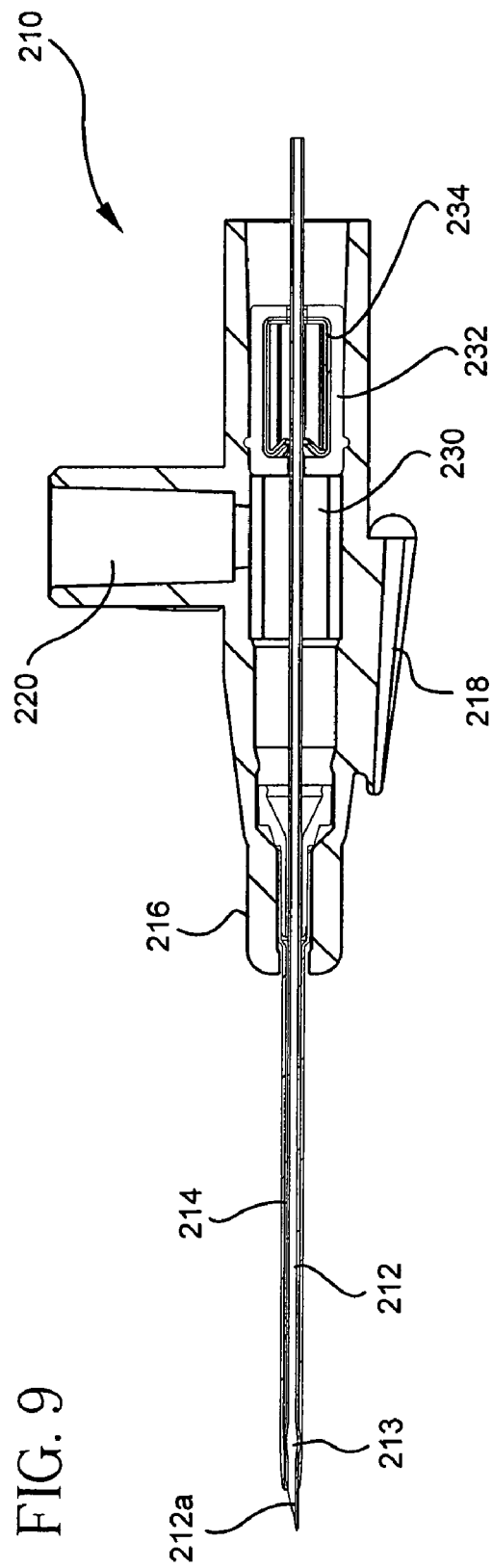
FIG. 9 is a sectional view of another embodiment of a catheter assembly of the present invention prior to insertion of a catheter.
Figure 10:
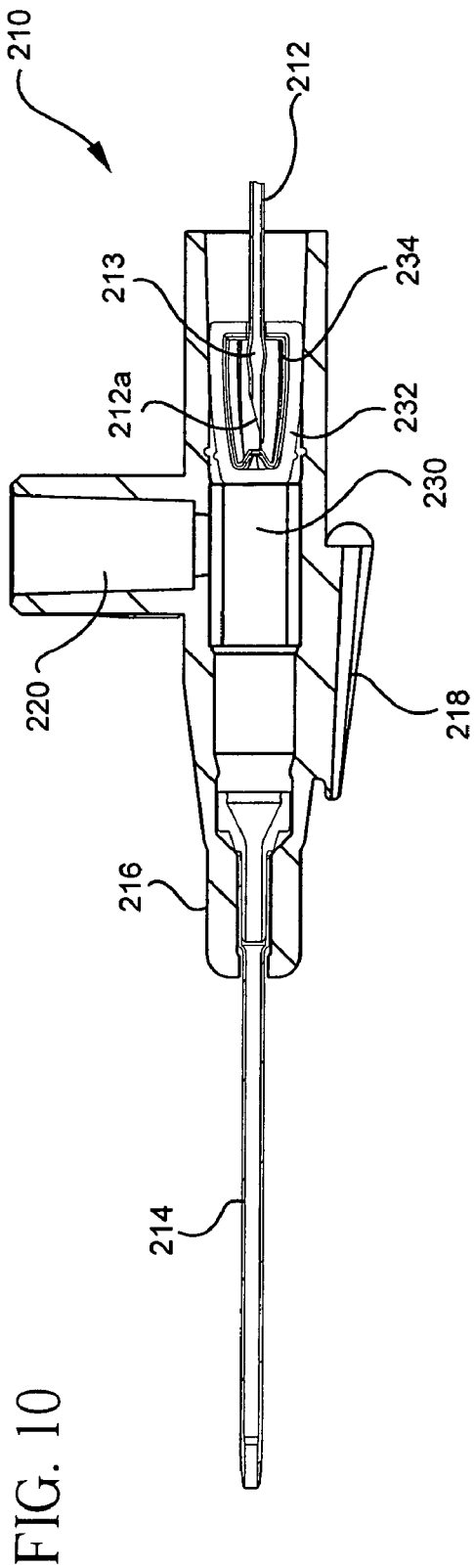
FIG. 10 is a sectional view of the catheter assembly of FIG. 9 after insertion of the catheter and as a needle is being withdrawn.

FIGS. 9 and 10 are sectional views of an alternative embodiment of a catheter assembly of the present invention. Catheter assembly 210, as shown in FIG. 9, is similar to catheter assembly 10 of FIGS. 1-4, and includes needle 212 having needle tip 212a and bump 213, catheter 214, catheter hub 216, wing 218 and port 220. Catheter hub 216 includes port septum 230, integrated septum 232 and tip shield 234. As shown in FIG. 9, tip shield 234 is in the open position because needle 212 is received through it and needle tip 212a is distal to tip shield 234. Tip shield 234 is similar to tip shield 134 of FIGS. 7 and 8, and includes a second layer of resilient fingers. It is recognized that a tip shield with only a single layer of resilient fingers, similar to tip shield 34 of FIGS. 2-6, may also be used in catheter assembly 210.

Figure 9A:
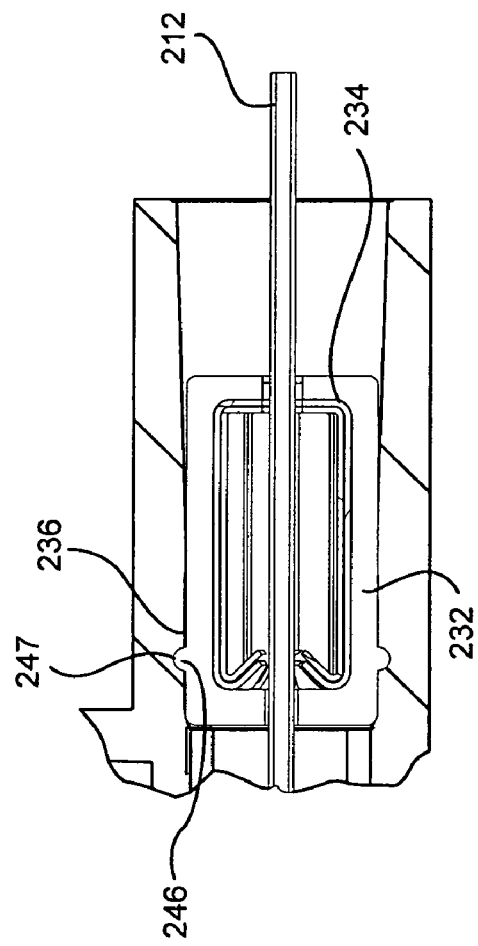
FIG. 9A is an exploded view of a portion of FIG. 9 showing another embodiment of an integrated septum and tip shield in an open position.

FIG. 9A is an exploded view of a portion of catheter assembly 210 of FIG. 9 showing integrated septum 232 and tip shield 234 in the open position. Septum 232 includes feature 246 formed on an outer surface of septum 232. Feature 246 is formed around an outer circumference of septum 232, and is configured to engage with inverse feature 247, shown in FIG. 9A as an annular groove, formed on inner surface 236 of catheter hub 216. Septum 232 may be configured to expand outward when needle 212 moves tip shield 234 into an open position, causing feature 246 to engage with inverse feature 247 formed on inner surface 236 of catheter hub 216, thus locking septum 232 into place within catheter hub 216.

Figure 10A:
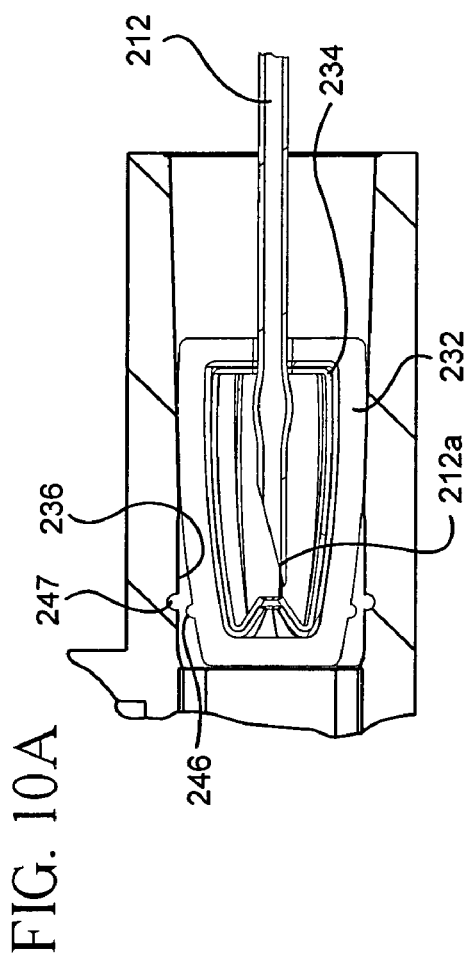
FIG. 10A is an exploded view of a portion of FIG. 10 showing the integrated septum and tip shield of FIG. 9A in a closed position.

FIG. 10 shows catheter assembly 210 of FIG. 9 after needle 212 has been withdrawn from catheter 214, but before needle 212 is completely withdrawn from catheter hub 216. FIG. 10A is an exploded view of a portion of FIG. 10 showing tip shield 234 in the closed position. Once needle tip 212a is withdrawn into tip shield 234, tip shield 234 moves to a closed position and septum 232, including feature 246, disengages from inner surface 236 of catheter hub 216. Septum 232 may then be easily removed from catheter hub 216 with needle 212. As shown in FIGS. 10 and 10A, feature 246 of septum 232 completely disengages from catheter hub 216 once tip shield 234 is in the closed position. However, it is recognized that feature 246 may still have some engagement with catheter hub 216 when tip shield 234 is in the closed position, so long as there is reduced engagement. The reduced engagement causes a reduction in force required to remove septum 232 from catheter hub 216, as compared to when tip shield 234 is in the open position.

As shown in FIGS. 9A and 10A, feature 246 is a protrusion extending around the outer circumference of septum 232. Feature 246 may include other types of features formed on septum 232, instead of or in addition to a protrusion, which are configured to mate with an inverse feature on an inner surface of catheter hub 216.

Catheter assembly 210 of FIGS. 9 and 10, similar to catheter assembly 10 of FIGS. 1-4, includes a ported catheter with port 220. Again, it is recognized that the present invention may be used with any type of catheter, including a straight catheter. The integrated septum and needle tip shield is designed to be secured inside any type of catheter hub and be easily removable with a needle after a tip of the needle is protected inside the tip shield.

In yet another embodiment, an integrated septum and tip shield unit may include a septum that is not configured to be expandable and retractable in order to engage and disengage with the inner surface of the catheter hub, but is instead simply held in place within the catheter hub by a balance of frictional forces. This embodiment, as compared to the embodiments described above, may be more sensitive to dimensional variations of the catheter hub or septum and tip shield. In the embodiments described above and shown in FIGS. 2-5, and 7-10, the septum automatically disengages with the catheter hub when the tip shield closes, and the septum is thus easily removable from the catheter hub as the needle is withdrawn from the catheter hub. Thus, the clinician may likely not notice or feel the separation between the septum and the catheter hub. However, in the alternative embodiment in which the septum is frictionally held in place within the catheter hub, the clinician may need to pull the needle with some additional force to remove the septum from the catheter hub.

Tip shield 24 of the present invention, as described above and shown in FIGS. 2-6, may preferably be formed out of metal, although other materials may be used. The tip shield may be formed from a flat piece of sheet metal. A plurality of cuts may be formed in the metal, with the cuts arranged parallel to one another, to form a plurality of segments. The metal may then be formed into a hollow cylindrical tube with the cuts configured longitudinally on the tube. At one end of the tube, a portion of each segment may be bent downward into an inner diameter of the tube to form the plurality of resilient fingers.

To form the double layer embodiments of tip shields 134 and 234, as shown in FIGS. 7-10, a second piece of sheet metal may be similarly formed, provided that the tube formed from the second piece of sheet metal has a larger diameter than the diameter of the tube formed from the first piece of sheet metal. Thus, the second tube may be inserted over the first tube to form outer body portion 136 of tip shield 134. Tip shield 234 may be similarly formed.

The embodiments of the septum, as described above and shown in FIGS. 2-5 and 7-10, may preferably be formed from an elastomer. The septum may be formed by injection or compression molding, in which the mold is configured to form an opening at a proximal end of the septum. After the septum is formed, a slit or puncture may be added at a distal end of the septum.

The integrated septum and needle tip shield may be formed by either inserting the tip shield into a previously molded septum or molding the septum directly over the tip shield. In a preferred method, the tip shield is inserted into a previously molded septum. Because the septum is preferably made from an elastomeric material, so long as the septum has an opening at the proximal end and a hollow interior, the tip shield may be forced through the opening into the interior of the septum. The original size of the opening and the hollow space of the interior may not be required to be as large as the tip shield, since the septum may be configured to expand to receive the tip shield inside the septum.

It is recognized that tip shields having a single or double layer of fingers may be formed using additional or alternative methods to those described above. It is also recognized that the septa described above may be formed using alternative processes. Moreover, additional methods of forming the integrated septum and needle tip shield are within the scope of the invention.

To assemble a catheter assembly similar to catheter assembly 10 of FIGS. 1-4, catheter 14 may be attached to catheter hub 16, prior to placement of needle 12 through catheter hub 16 and catheter 14. The integrated unit of septum 32 and tip shield 34 may be mounted onto a proximal end of needle 12. The distal end of needle 12, having needle tip 12a and feature 13, may then be inserted into the proximal end of catheter hub 16 and consequently threaded through catheter hub 16 and catheter 14 until needle tip 12a is extending out through the distal end of catheter 14 (see FIG. 1). As needle 12 is threaded through catheter hub 16 and catheter 14, septum 32 and tip shield 34 are inserted into catheter hub 16. Because tip shield 34 is the open position due to needle 12 passing through it, septum 32 may expand outward. Thus, some force may be required to insert septum 32 into catheter hub 16. Needle hub 24 (see FIG. 1) may be inserted onto the proximal end of needle 12 before or after needle 12 is threaded through catheter hub 16. It is recognized that an automated manufacturing process may preferably be implemented for the assembly of catheter assembly 10.

The additional embodiments described above, including integrated septum 132 and tip shield 134 of FIGS. 7 and 8, and catheter assembly 210 of FIGS. 9 and 10, may be assembled using the preferred methods described above. However, it is recognized that additional methods of forming the integrated septum and tip shield, as well as assembling the catheter assembly, are within the scope of the present invention.

Although the present invention has been described with reference to preferred embodiments, workers skilled in the art will recognize that changes may be made in form and detail without departing from the spirit and scope of the invention.

The invention claimed is:

1. An integrated septum and needle tip shield apparatus for use in a catheter assembly having a needle, a catheter and a catheter hub, the apparatus comprising:

an elastomeric septum configured to removably engage with an inner surface of the catheter hub, the septum having a proximal end wall a distal end wall, a distal end wall, and an outer side wall extending between the proximal and distal end walls; and a tip shield secured inside the septum, the septum encases the tip shield in proximal, distal, and radial directions, the tip shield is configured to move between an open position in which a tip of the needle is distal of the tip shield and the needle and tip shield force the septum to expand radially outward so that the outer side wall of the septum engages and interfaces with the inner surface of the catheter hub and a closed position in which the tip of the needle is protected, completely enclosed, and essentially sealed within both the tip shield and the septum and the septum returns to an original shape and correspondingly the outer side wall of the septum disengages from the inner surface of the catheter hub so as to allow the needle, the septum, and the tip shield to be withdrawn together from the catheter hub;

wherein the tip shield has a plurality of resilient fingers at a distal end thereof configured to be contacted and pushed radially outward by the needle when the tip of the needle is distal of the tip shield, and to retract radially inward when the tip of the needle is withdrawn past the resilient fingers;

and wherein the resilient fingers act with the needle to engage and disengage the septum from the inner surface of the catheter hub.

2. The apparatus of claim 1, wherein the plurality of resilient fingers includes at least four fingers.

3. The apparatus of claim 1, wherein the plurality of resilient fingers includes at least seven fingers.

4. The apparatus of claim 1, wherein the outer sidewall of the septum has a protrusion configured to be removably engageable with a feature on the inner surface of the catheter hub.

5. The apparatus of claim 1, wherein the tip shield further comprises an outer layer of fingers that are configured to overlay the resilient fingers.

6. The apparatus of claim 1, wherein the septum is configured to essentially seal fluid inside the catheter hub during insertion of the catheter into a vessel, and essentially seal the tip shield and the tip of the needle to prevent fluid leakage from the needle after the tip of the needle is inside the tip shield.

7. A catheter assembly comprising:
a catheter;
a catheter hub attached to the catheter;
a needle hub;
a needle having a distal end, a proximal end, and a tip at the distal end, wherein the needle is attached to the needle hub at a proximal end, inserted through the catheter hub and the catheter, and configured to be removed from the catheter hub and the catheter;
a tip shield having a distal end, a proximal end, and a plurality of resilient fingers at the distal end, wherein the fingers are configured to be in an open position when the needle is inserted through the catheter and a closed position when the tip of the needle is inside the tip shield; and
an elastomeric septum having a proximal end wall, a distal end wall, and a generally cylindrical outer side wall extending between the proximal and distal end walls, the septum surrounding the tip shield in proximal, distal and radial directions, wherein the needle and tip shield force the outer side wall of the septum to expand radially outward and engage and form a seal with an inner surface of the catheter hub when the fingers of the tip shield are in the open position, and wherein when the tip shield is in the closed position the septum encloses and essentially seals both the tip shield and the tip of the needle and returns the outer side wall to an original shape and correspondingly disengages from the inner surface of the catheter hub so that the septum is removable along with the needle from the catheter hub; and wherein the resilient fingers act with the needle to engage and disengage the septum from the inner surface of the catheter hub.

8. The catheter assembly of claim 7, wherein the fingers are configured to prevent distal movement of the needle when the tip of the needle is inside the tip shield.

9. The catheter assembly of claim 7, wherein a portion of the needle has an increased diameter to prevent further proximal movement of the needle once the tip of the needle is inside the tip shield.

10. The catheter assembly of claim 7, wherein the outer side wall of the septum includes a feature configured to be engageable with an inverse feature on the inner surface of the catheter hub.

11. The catheter assembly of claim 7, wherein the septum is configured to seal fluid inside the catheter hub when the outer side wall of the septum is engaged with the inner surface of the catheter hub.

12. The catheter assembly of claim 7, wherein the plurality of resilient fingers includes at least four fingers.

13. The catheter assembly of claim 7, wherein the tip shield is formed from metal.

14. The catheter assembly of claim 7, wherein the septum is formed from an elastomer.

15. The catheter assembly of claim 7, wherein the resilient fingers of the tip shield form a first layer of fingers, and the tip shield comprises a second layer of resilient fingers that are angularly offset from the first layer of fingers and configured to overlay the first layer of fingers.

* * * * *